United States Patent [19]

Higo et al.

[11] Patent Number: 5,289,387
[45] Date of Patent: Feb. 22, 1994

[54] METHOD FOR MEASURING STRESS

[75] Inventors: Yakichi Higo, 3-1-101, Yakumo 5-chome, Meguro-ku, Tokyo; Junichiro Matsuoka, Machida; Jun Kiyoshige, Atsugi; Kazuhiko Tsukaguchi, Sagamihara; Shigenori Kazama, Yokohama, all of Japan

[73] Assignees: Nissan Motor Company, Limited, Yokohama; Yakichi Higo, Tokyo, both of Japan

[21] Appl. No.: 554,536

[22] Filed: Jul. 20, 1990

[30] Foreign Application Priority Data

Jul. 20, 1989 [JP] Japan ................................ 1-186083

[51] Int. Cl.⁵ ............................................. G06F 15/20
[52] U.S. Cl. .................................... 364/508; 364/553; 73/801; 73/806
[58] Field of Search ............ 364/508, 553, 576; 73/12, 801, 806, 579, 582, 1 D; 333/72

[56] References Cited

U.S. PATENT DOCUMENTS

| | | | |
|---|---|---|---|
| 3,973,112 | 8/1976 | Sloane | 364/553 |
| 4,067,060 | 1/1978 | Poussart et al. | 364/576 |
| 4,096,456 | 6/1978 | Coussot et al. | 333/72 |
| 4,399,702 | 8/1983 | Suzuki | 73/597 |
| 4,539,847 | 9/1985 | Paap | 73/579 |
| 4,694,698 | 9/1987 | Miyajima | 73/570 |
| 4,702,111 | 10/1987 | Holland | 73/579 |
| 4,854,172 | 8/1989 | Lemaster | 73/801 |
| 4,854,494 | 8/1989 | von Raben | 73/582 |
| 4,969,106 | 11/1990 | Vogel et al. | 364/508 |
| 4,991,124 | 2/1991 | Kline | 73/579 |
| 5,000,030 | 3/1991 | Umeda et al. | 73/1 D |
| 5,038,295 | 8/1992 | Husband et al. | 364/508 |
| 5,065,331 | 11/1991 | Vachon et al. | 364/508 |
| 5,069,071 | 12/1991 | McBrien et al. | 73/579 |

OTHER PUBLICATIONS

Ultrasonics, vol. 25, May 1987 pp. 160–165–Ultrasonic Study on the Change and Elastic Anisotropy etc.
Ultrasonic Testing J. S. Zilard 1982, pp. 437–458.
Materialprufung 19 No. 2 Feb. 1977, pp. 58–64.
IEEE Transactions on Sonics and Ultrasonics vol. SU-30, No. 4, Jul. 1983 "Acoustic Parameters of Commercial etc.".

*Primary Examiner*—Jack B. Harvey
*Assistant Examiner*—Ellis B. Ramirez
*Attorney, Agent, or Firm*—Foley & Lardner

[57] ABSTRACT

Stress in a substance is measured by utilizing the transfer characteristics of elastic waves, such that elastic waves input to a substance are displaced by the stress load within the substance. Waves input to the substance and output therefrom by transmission or reflection are compared by fast fourier transform analysis, obtaining a wave attenuation factor quantifying the magnitude of stress in the substance.

20 Claims, 2 Drawing Sheets

METHOD FOR MEASURING STRESS

BACKGROUND OF THE INVENTION

1. Field of the Invention

The present invention relates generally to a method for measuring stress magnitude distributed, more particularly, it relates to a method for quantitative measurement of stress in a substance which is formed of materials such as metal or resin, without damaging the substance.

2. Description of the Background Art

Generally external stress, such as tensile, shear, cleavage and peeling stress, and internal stress frequently occur in substances formed using adhesion techniques, particularly using thermal adhesion techniques. As for measuring these stresses, several methods are well known in the art. For example, in a substance formed of metals, X-Ray irradiation to the substance has been applied for measuring stress utilizing the properties of displacement of a reflection grading which is caused by uniform strain when crystals of the tested substance are subjected the stress. On the other hand, electrical measurement has also been applied utilizing the properties of the slight change of electrical resistance of an attached strain gauge when the tested substance is subjected the strain. In a substance formed of resins, the cracking properties of solvents have been utilized for measuring stress. A solvent is infused into the stressed substance then the time necessary for the generation of cracking and the size of cracks are analyzed. On the other hand, treatments such as applying a predetermined surface stress to a substance by curving it at predetermined angle are performed. Then a solvent is dropped on the curved substance. The cracking generation caused by this predetermined stress is compared to that of sample of the substance having an unknown quantity of stress. Other methods utilizing of cracking properties of the solvent have also been applied, however, all these methods estimate the stress relatively by cracking occurrence when various solvents contact with a substance having an unknown quantity of stress.

However, the methods as mentioned above require predetermined sizes of test pieces, therefore local stress measurement or estimation of actual parts, products or materials can not be accomplished easily. Additionally, measurement becomes very complicated so the time consumed in measurement becomes excessive. On the other hand, as measurements utilizing the cracking properties of solvents are essentially measurements of the breaking point of the substance relative a particular solvent, measurement of stress without breaking the tested substance can not be accomplished. Furthermore, the stress values obtained by the cracking methods as above yield results of relative estimation having only diagrammatic accuracy in the detection of stress magnitude, giving values such as high, medium and low, therefore, accurate quantification of stress is not possible.

SUMMARY OF THE INVENTION

It is therefore the principal object of the present invention to provide a method for measuring stress distributed in a substance.

It is another object of the present invention to provide a method for measuring stress in substances such as parts, products or materials at a desired portion thereon regardless of their configurations, without preparing special test pieces.

It is additional object of the present invention to provide a simple method for measuring stress in a short period of time.

It is further object of the present invention to provide a method for quantitative local measurement of stress in a substance.

It is furthermore object of the present invention to provide a method for measuring stress in a substance without damaging the substance.

It is further object of the present invention to provide an apparatus for measuring stress in a substance.

A method for measuring stress distributed in a substance comprises the steps of inputting elastic waves to the substance, comparing output waves which are transmitted and/or reflected from the substance, displaced by the stress, to the input waves, and analyzing an attenuation factor of the input waves and the displaced output waves obtained as a transfer function of the elastic waves, the function associated with a magnitude of stress contained in the substance with a quantitative measurement without damaging the substance and without need for preparing special preparing test pieces for measurement.

The analyzing of the attenuation factor can be done by processing a fast fourier transformation which converts the transfer function from time area to frequency area.

Inputting the waves to the substance may be accomplished using a first transducer, and receiving the output waves may be accomplished using a second transducer.

The output waves may be received by plurality of transducers for relative comparison to each other.

The inputting step and the receiving step may be accomplished by a common transducer.

A plurality of transducers may be sequentially activated.

The transfer function can be obtained by a linear or non-linear analysis of frequency dependent wave attenuation factor.

Analysis may be accomplished at a frequency or frequency area selected in a range from 0.1 KHz to 10 MHz, and by comparing the absolute or the relative values of the transfer function.

The method may be also comprises a step of measuring local stress in the substance by means of fixing the measuring point. On the other hand, the method may further comprises a step of measuring stress distribution in the substance by means of scanning a measuring region.

An apparatus for measuring stress in a substance comprises a signal generating means for generating an electric signal, a first transducing means for converting the electric signal to an elastic wave and inputting the wave into the substance, a second transducing means for receiving a wave output from the substance and converting the wave to an electric signal, an amplifying means for amplifying the output electric signal, a recording means for recording the electric signals transferred from the generating means and from the amplifying means, a analyzing means for comparing the recorded signals and analyzing the wave attenuation factor of a transfer function of the elastic waves in the frequency area, and a computer for conducting commands to the whole the apparatus, the computer cooperating with display means for displaying the obtained values visibly as a quantitative magnitude of the stress. The analyzing means may transform the signals in time area to frequency area via the processing of a fast fourier transformation.

BRIEF DESCRIPTION OF THE DRAWINGS

The present invention will be understood from the detailed description given hereinbelow and from the accompanying drawings of the preferred embodiments which are given for explanation and understanding only and are not intended to imply limitation to the invention.

In the drawings.

DETAILED DESCRIPTION OF THE PREFERRED EMBODIMENT

Stress in a substance is measured by taking advantage of the transfer characteristics exhibited by elastic waves within the substance. Elastic waves such as ultrasonic waves irradiated to a substance formed of materials such as polycarbonates or acryl resin are displaced by load stress in the substance. Waves input into a portion of the substance and the waves subsequently output from the substance, such as transmitted and/or reflected waves are compared and analyzed.

The substances tested may be selected from metals or resins. The measurement apparatus of the invention can be applied to any parts or products.

Estimation of transfer characteristics may be accomplished by linear or non-linear analysis of frequency dependent on the wave attenuation factor. The preferable frequency may be selected in a range from 0.1 KHz and 10 MHz. Absolute or relative measurement values may be compared and estimated in this frequency range.

The present measurement apparatus can be utilized for measuring local stress by measuring at a fixed point, or can be utilized for measuring stress distribution by scanning.

One embodiment of the stress measurement apparatus of the present invention has a fundamental structure including a pulsar transducer for inputting waves to irradiate a portion of a substance, a sensor transducer for receiving output waves which are transmitted and/or reflected from the substance, and an analyzing means for quantitative measurement of stress in the substance (without damage) by analyzing the transfer characteristics of transmitted and/or reflected waves received by the sensor transducer.

Figure 1:
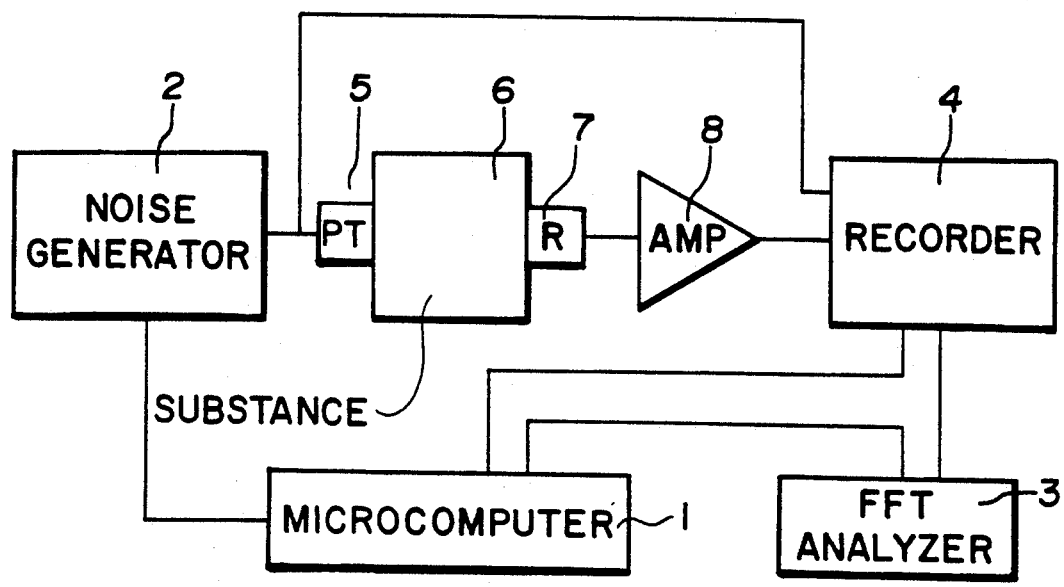
FIG. 1 is a schematic block diagram illustration of one embodiment of a stress measurement apparatus according to the present invention.

Referring now to FIG. 1 showing a schematic block diagram which indicates the fundamental structure of above mentioned embodiment, numeral 1 generally designates a microcomputer which controls whole circuit. A loop circuit is formed through the microcomputer 1 via a measuring port. The computer 1 is connected with a noise generator 2, a Fast Fourier Transform (FFT) analyzer 3 and a recorder 4, respectively.

The computer 1, the FFT analyzer 3 and the recorder 4 or such comprise the analyzing means.

Electric signals of pseudo noise are generated in the noise generator 2. The generator 2 is connected with a pulsar transducer (PT) 5 for inputting elastic waves into a portion of the substance 6. Signals generated in the generator 2 are not only transferred to the pulsar transducer 5 but also to the recorder 4. On the other hand, a sensor transducer (R) 7 which receives transmitted and/or reflected waves output from the substance 6 is connected with the recorder 4 via an amplifier 8.

Figure 2:
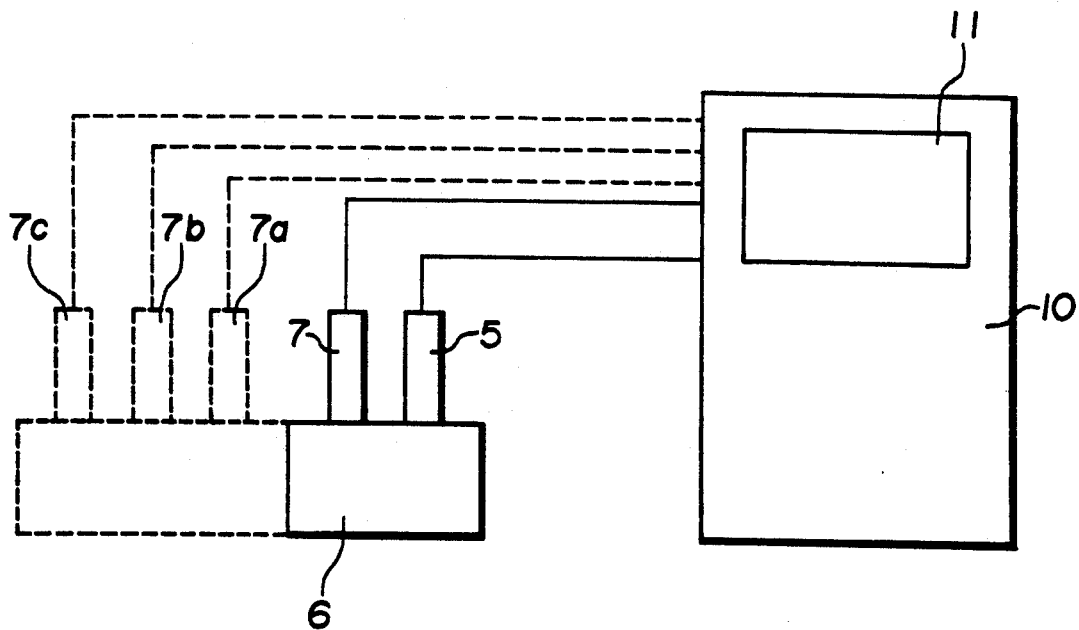
FIG. 2 is a representative schematic for the stress measurement apparatus illustrated in FIG. 1.

Referring now to FIG. 2 showing the employment of the apparatus having the fundamental structure abovementioned, the noise generator 2, the FFT analyzer 3, the recorder 4 and the amplifier 8 are assembled in an apparatus body 10 with the microcomputer 1. The pulsar transducer 5 and plurality of sensor transducers 7, 7a, 7b, and 7c are individually adhered on the surface of the substance 6 at desired measuring points respectively, while concurrently being connected with the body 10 via lead lines. When analyzing the transfer characteristics of the waves output from the substance 6, relative comparison may be done by comparing the value obtained from two transducers such as 7 and 7a. An waveform display 11 is mounted on the body 10.

The FFT analyzer 3 of this embodiment is an apparatus for processing Fourier transformations of time data to frequency data. Input signal are A-D converted and memorized in a buffer memory, then the data is transformed by an FFT (fast Fourier transform) algorithm in an internal computer which processes the frequency analysis.

The stress measurement apparatus of FIGS. 1 and 2 operates as follows;

Electric signals generated from pseudo noise in the noise generator 2 are transferred to the pulsar transducer 5 at the command of the microcomputer 1. At the transducer 5, the signals are converted to elastic waves and input into the substance 6 at a specified portion. The elastic waves are transmitted through the substance 6. The transmitted waves are received and detected by the sensor transducer 7 at another portion of the substance 6. The waves are then converted to electric signals again at the transducer 7, amplified at the amplifier 8, and transferred to the FFT analyzer 3 via the recorder 4. In addition, the pseudo noise electric signals generated in the noise generator 2 are also transferred to the recorder 4, directly recorded therein and transferred to the FFT analyzer 3. Both signals are, that is the signals from the the amplifier 8 and the signals transferred directly from the generator 2, are compared at the FFT analyzer 3, thus the transfer function of waves is calculated.

The transfer function of the processing signals are transferred from the FFT analyzer 3 to the microcomputer 1 concurrently being displayed on such as a CRT for example. In the microcomputer 1, the transfer function is processed and integrated at a desired frequency intermittance. The integrated value of the function and the individual value thereof at each frequency are displayed on the display as a measurement value. Thus, stress in the substance 6 can be represented visibly.

Figure 3:
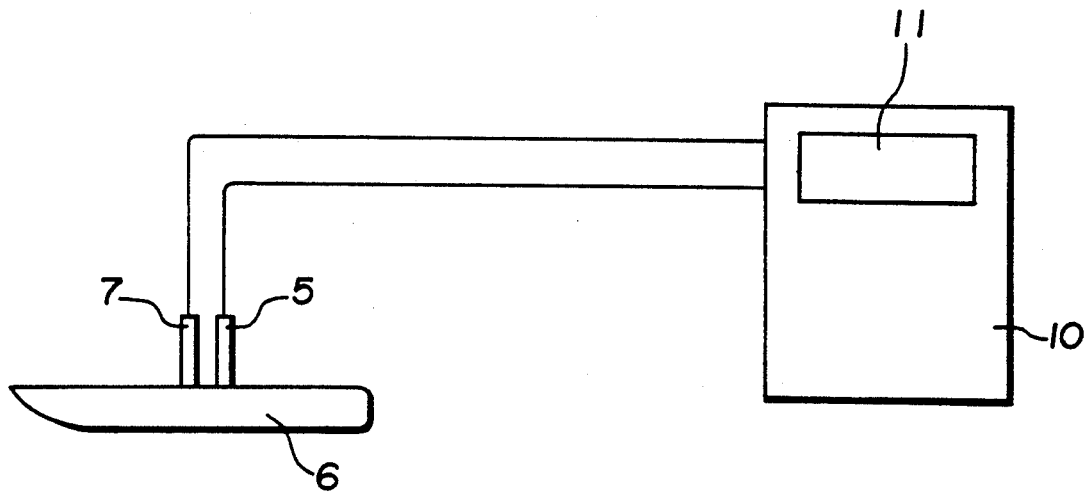
FIG. 3 is a representative schematic of another embodiment for measuring stress in a rear combination lamp of an automotive vehicle according to the stress measurement apparatus of the present invention.
Figure 4:
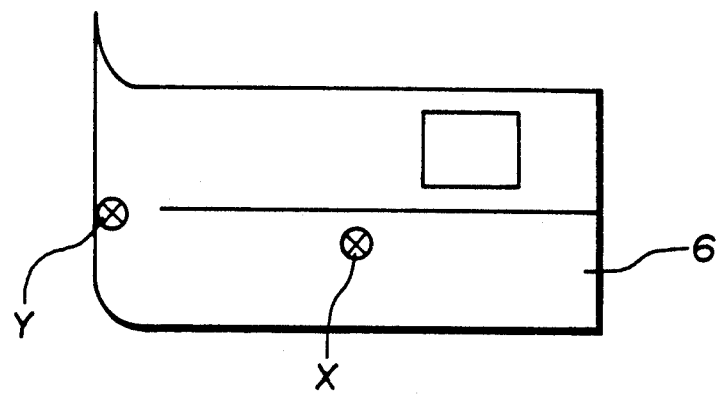
FIG. 4 (a) and (b) are representative schematics showing measuring points on the rear combination lamp illustrated in FIG. 3.
Figure 4:
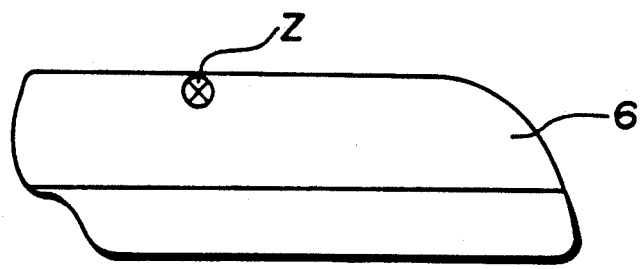

FIGS. 3 to 5 show another embodiment of the stress measurement apparatus according to the present invention.

In an automotive vehicle, rear combination lamps are susceptible to environmental stress and cracking frequently occurs. FIG. 3 is a stress measurement apparatus particularized for the measurement of stress in rear combination lamps for automobiles. The lamps are formed of polyacrylic resin and are utilized as exterior parts of automotive vehicles. An apparatus body 10 and a display 11 are the same as those of FIG. 2. A pulsar transducer 5 and a sensor transducer 7 are connected with the body 10 by lead lines which extend from the apparatus body 10. Measurement positions such as X, Y, Z are determined as shown in FIGS. 4 (a) and (b). These positions are determined to have 3 cm of intermittance, respectively. The pulsar transducer 5 and the sensor transducer 7 are adhered to their respective positions on the lamp (substance) 6 via silicon grease. Here, the position of X is a portion which is predicted to have relatively small internal strain where it is subjected no thermal welding and cementing, the position Y is a portion which is predicted to have relatively large internal strain due to the thermal welding and the position Z is a portion which is predicted to have small internal strain due to cementing using a hot-melting type adhesive.

Once the pseudo noise electrical signals are transferred to the pulsar transducer 5, the signals are converted to elastic waves. The waves are then input to the rear combination lamp 6 via the portion of the transducer 5 adhered on the surface of the lamp 6, transmitted to the lamp 6, and then are output from the lamp 6 and received by the sensor transducer 7 to be subsequently amplified at an amplifier in the apparatus body 10, to finally be transferred to the FFT analyzer via the recorder, both of which are also within the body 10. At the FFT analyzer, the signals amplified by the amplifier and the electric signals from the noise generator (also in the apparatus body 10) are compared, a transfer function of f(x) is obtained. The obtained function is integrated in a frequency range of 200 KHz to 500 KHz. Increments Δf(x) obtained by the integration are defined as the measurement value.

The obtained measurement values at each position X, Y and Z of the lamp 5 are shown in the following Table 1.

TABLE 1

| Measurement Position | Means of Adhesion | Predicted Magnitude of Stress | Stress Value Δf(x) db |
|---|---|---|---|
| X | — | Small | 3.4 |
| Y | Thermal Welding | Large | 8.9 |
| Z | Adhesive | Small | 4.6 |

As clearly shown in the above Table 1, the stress in the measurement position Y which was predicted to have relatively large internal strain because of the thermal welding indicated a value approximately 2 times that of both X and Z, which were predicted to have relatively small internal strain. The measurement was be accomplished without damage to the rear combination lamp which was an actual automotive part unmodified for testing. Furthermore, the magnitude of the stress could be quantified at each measurement position.

Additionally, in the above embodiment, both transducers 5 and 7 were adhered to the surface of the substance 6, however, they may alternatively be passed along the surface of the substance 6 for scanning thereof. Distribution of stress in the substance can be obtained by scanning. Further to say, two transducers are utilized as pulsar and sensor transducers in the above embodiment, however, similar results can be obtained when using a plurality of sensor transducers can be used for providing a relative value from the individually obtained values. Alternatively the pulsar and the sensor functions may be shared by a single transducer. A transducer of the electric circuit of FIGS. 1 and 2 may be changed alternately switched from a pulsar function to a sensor function by switching the electric circuit appropriately.

According to the present invention, stress in a substance can be measured without damage or preparation of test pieces by elastic wave irradiation to a portion of the substance surface, and subsequently analyzing the waves output from the surface, which waves are changed by the internal stress. Therefore, the measurement can be applied not only for test pieces but for any configuration of substances of manufactured articles such as parts, products or materials. Additionally, measurement can be accomplished in a very short time as the method for measurement is simplified. Furthermore, according to the present method, quantifying of the stress is possible.

While the present invention has been disclosed in terms of the preferred embodiments in order to facilitate better understanding thereof, it should be appreciated that the invention can be embodied in various ways without departing from the principle thereof. Therefore, the invention should be understood to include all possible embodiments and modifications to shown embodiments which can be embodied without departing from the principle of the invention as set out in the appended claims.

What is claimed is:

1. A method for measuring stress magnitude distributed in a substance comprising the steps of:
   inputting elastic waves to a substance so as to irradiate a desired portion thereof;
   receiving output waves which are transmitted and/or reflected from said substance;
   comparing said input waves with said output waves associated with analyzing attenuation factors of said input and output waves being converted into frequency values to define transfer functions of said waves; and
   defining said stress magnitude as an increment of said transfer functions between said output and input waves for providing a quantitative measurement of said stress.

2. The method for measuring stress magnitude distributed in a substance as set forth in claim 1, wherein said inputting step and said receiving step are executed by a common transducer.

3. The method for measuring stress magnitude distributed in a substance as set forth in claim 1, wherein said transfer function is obtained by linear analysis of frequency dependent on the wave attenuation factor.

4. The method for measuring stress magnitude distributed in a substance as set forth in claim 1, wherein said function is obtained by non-linear analysis of frequency dependent on said wave attenuation factor.

5. The method for measuring stress magnitude distributed in a substance as set forth in claim 1, wherein said method includes a step of measuring local stress in said substance by means of a fixed measuring point.

6. The method for measuring stress magnitude distributed in a substance as set forth in claim 1, wherein said method includes a step of measuring a stress distribution in said substance by means of scanning a measuring region.

7. The method for measuring stress magnitude distributed in a substance as set forth in claim 1 further comprising;
inputting said waves to said substance via a first transducer, and receiving said output waves via a second transducer.

8. The method for measuring stress magnitude distributed in a substance as set forth in claim 1, wherein said output waves are received by a plurality of transducers for relative comparison to each other.

9. The method for measuring stress magnitude distributed in a substance as set forth in claim 8, wherein said plurality of transducers are sequentially activated.

10. The method for measuring stress magnitude distributed in a substance as set forth in claim 1, wherein said analyzing step is accomplished by fast fourier transformation processing which converts said transfer function from time area to frequency area.

11. The method for measuring stress magnitude distributed in a substance as set forth in claim 10, wherein said analysis is carried out at a frequency selected in a range from 0.1 KHz to 10 MHz.

12. The method for measuring stress magnitude distributed in a substance as set forth in claim 10, wherein said analysis is carried out by comparing absolute values of said transfer function.

13. The method for measuring stress magnitude distributed in a substance as set forth in claim 10, wherein said analysis is carried out by comparing relative values of said transfer function.

14. An apparatus for measuring stress magnitude distributed in a substance, comprising:
a signal generating means for generating an input electric signal;
a first transducing means for converting said input electric signal to elastic waves and inputting said waves to a substance so as to irradiate a desired portion thereof;
a second transducing means for receiving output waves from said substance and converting said output waves to an output electric signal;
an amplifying means for amplifying said output electric signal to obtain an amplified electric signal;
a recording means for recording both of said input and amplified electric signals transferred from said generating means and said amplifying means,
an analyzing means for comparing said recorded signal from the generating means with that from the amplifying means associated with analyzing wave attenuation factors of both of said input and amplified electric signals being converted into frequency values to define transfer functions of said input and amplified electric signals,
a display means for displaying the frequency values of said transfer functions as a quantitative value of said stress, and
a computer for calculating an increment of a transfer function between said input and amplified electric signals to define stress magnitude distributed in said substance, and for issuing commands to said signal generating means, said first and second transducing means, said amplifying means, said recording means, said analyzing means and said display means.

15. The apparatus for measuring stress magnitude distributed in a substance as set forth in claim 14, wherein said analyzing means transforms said signals from time area to frequency area by fast fourier transformation processing.

16. The apparatus for measuring stress magnitude distributed in a substance as set forth in claim 14, wherein said second transducing means includes a plurality of transducers for relative comparison of said output waves to each other.

17. The apparatus for measuring stress magnitude distributed in a substance as set forth in claim 14, wherein said first and said second transducing means are incorporated in a common transducer.

18. The apparatus for measuring stress magnitude distributed in a substance as set forth in claim 16, wherein said plurality of transducers are sequentially activated.

19. A method for measuring stress magnitude distributed in a substance, comprising the steps of:
inputting elastic waves to a substance so as to irradiate a desired portion thereof;
receiving output waves which are transmitted and/or reflected from said substance;
comparing said input waves with said output waves associated with analyzing attenuation factors of said input and output waves being converted into frequency values to define transfer functions of said waves;
processing the transfer functions by fast fourier transformation such that the transfer functions are converted from a time domain to a frequency domain; and
defining said stress magnitude in said substance as an increment of said transfer functions between said output and input waves for providing a quantitative measurement of said stress.

20. An apparatus for measuring stress magnitude distributed in a substance, comprising
a signal generating means for generating an input electric signal;
a first transducing means for converting said input electric signal to an elastic wave and inputting said wave to a substance so as to irradiate a desired portion thereof;
a second transducing means for receiving a wave output from said substance and converting said wave to an output electric signal;
an amplifying means for amplifying said output electric signal to obtain an amplified electric signal;
a recording means for recording both of said input and amplified electric signals transferred from said generating means and said amplifying means;
an analyzing means for comparing said recorded signal from the generating means with that from the amplifying means associated with analyzing wave attenuation factors of both signals being converted into frequency values to define transfer functions of said input and amplified electric signals, said analyzing means processing the transfer functions by fast fourier transformation such that the transfer functions are converted from a time domain to a frequency domain;
a display means for displaying the frequency values of said transfer functions as a quantitative value of said stress; and
a computer for calculating an increment of said transfer function between said input and amplified electric signals to define stress magnitude distributed in said substance, and for issuing commands to said signal generating means, said first and second transducing means, said amplifying means, said recording means, said analyzing means and said display means.